United States Patent
Kramer et al.

(10) Patent No.: US 7,142,915 B2
(45) Date of Patent: Nov. 28, 2006

(54) APPARATUS AND METHOD FOR VENTRICULAR RATE REGULARIZATION

(75) Inventors: Andrew P. Kramer, Stillwater, MN (US); Jeffrey E. Stahmann, Ramsey, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 699 days.

(21) Appl. No.: 10/462,029

(22) Filed: Jun. 13, 2003

(65) Prior Publication Data

US 2004/0010295 A1    Jan. 15, 2004

Related U.S. Application Data

(63) Continuation of application No. 09/751,431, filed on Dec. 29, 2000, now abandoned.

(51) Int. Cl.
   *A61N 1/30* (2006.01)
(52) U.S. Cl. ............................................. 607/9
(58) Field of Classification Search ............... 607/9, 607/14, 17, 25, 28
   See application file for complete search history.

(56) References Cited

U.S. PATENT DOCUMENTS

| | | | |
|---|---|---|---|
| 3,857,399 A | 12/1974 | Zacouto | 128/419 P |
| 4,030,510 A | 6/1977 | Bowers | 128/419 PG |
| 4,059,116 A | 11/1977 | Adams | 128/419 PG |
| 4,163,451 A | 8/1979 | Lesnick et al. | 128/419 PG |
| 4,208,008 A | 6/1980 | Smith | 371/15 |
| RE30,387 E | 8/1980 | Denniston, III et al. | 128/419 |
| 4,432,360 A | 2/1984 | Mumford et al. | 128/419 PG |
| 4,503,857 A | 3/1985 | Boute et al. | 128/419 PG |
| 4,556,063 A | 12/1985 | Thompson et al. | 128/419 PT |
| 4,562,841 A | 1/1986 | Brockway et al. | 128/419 PG |
| 4,596,255 A | 6/1986 | Snell et al. | 128/697 |
| 4,791,936 A | 12/1988 | Snell et al. | 128/697 |
| 4,809,697 A | 3/1989 | Causey, III et al. | 128/419 PT |
| 4,830,006 A | 5/1989 | Haluska et al. | 607/4 |
| 4,869,252 A | 9/1989 | Gilli | 128/419 PG |
| 4,890,617 A | 1/1990 | Markowitz et al. | 128/419 PG |
| 4,905,697 A | 3/1990 | Heggs et al. | 128/419 PG |
| 4,917,115 A | 4/1990 | Flammang et al. | 128/419 PG |
| 4,920,965 A | 5/1990 | Funke et al. | 128/419 PG |
| 4,928,688 A | 5/1990 | Mower | 128/419 PG |
| 4,940,054 A | 7/1990 | Grevis et al. | 128/419 PG |
| 4,944,298 A | 7/1990 | Sholder | 128/419 PG |
| 4,944,928 A | 7/1990 | Grill et al. | 423/161 |
| 4,945,909 A | 8/1990 | Fearnot et al. | 128/419 PG |
| 4,972,834 A | 11/1990 | Begemann et al. | 128/419 |
| 4,998,974 A | 3/1991 | Aker | 128/419 PG |

(Continued)

FOREIGN PATENT DOCUMENTS

EP    0033418    12/1980

(Continued)

OTHER PUBLICATIONS

Clark, David M., et al., "Hemodynamic Effects of an Irregular Sequence of Ventricular Cycle Lengths During Atrial Fibrillation", *JACC*, vol. 30, No. 4, (Oct. 1997), 1039-1045.

(Continued)

*Primary Examiner*—George Manuel
(74) *Attorney, Agent, or Firm*—Schwegman, Lundberg, Woessner, & Kluth, P.A.

(57) ABSTRACT

A method and system for operating a cardiac rhythm management device which employs pacing therapy to regularize the ventricular rhythm. Such ventricular rate regularization may be employed with conventional bradycardia pacing, ventricular resynchronization therapy, or anti-tachyarrhythmia therapy.

23 Claims, 2 Drawing Sheets

U.S. PATENT DOCUMENTS

| | | | |
|---|---|---|---|
| 5,012,814 A | 5/1991 | Mills et al. | 128/691 |
| 5,042,480 A | 8/1991 | Hedin et al. | 128/419 PG |
| 5,085,215 A | 2/1992 | Nappholz et al. | 128/419 PG |
| 5,101,824 A | 4/1992 | Lekholm | 128/419 PG |
| 5,107,850 A | 4/1992 | Olive | 128/705 |
| 5,127,404 A | 7/1992 | Wyborny et al. | 128/419 P |
| 5,129,394 A | 7/1992 | Mehra | 128/419 PG |
| 5,139,020 A | 8/1992 | Koestner et al. | 128/419 PG |
| 5,144,949 A | 9/1992 | Olson | 128/419 PG |
| 5,156,147 A | 10/1992 | Warren et al. | 128/419 PG |
| 5,156,154 A | 10/1992 | Valenta, Jr. et al. | 128/661.09 |
| 5,179,949 A | 1/1993 | Chirife | 128/419 PG |
| 5,183,040 A | 2/1993 | Nappholz et al. | 128/419 PG |
| 5,184,614 A | 2/1993 | Collins et al. | 128/419 PG |
| 5,188,106 A | 2/1993 | Nappholz et al. | 128/419 PG |
| 5,193,535 A | 3/1993 | Bardy et al. | 128/419 D |
| 5,193,550 A | 3/1993 | Duffin | 129/697 |
| 5,197,467 A | 3/1993 | Steinhaus et al. | 128/419 PG |
| 5,207,219 A | 5/1993 | Adams et al. | 128/419 D |
| 5,282,836 A | 2/1994 | Kreyenhagen et al. | 607/4 |
| 5,284,491 A | 2/1994 | Sutton et al. | 607/17 |
| 5,292,339 A | 3/1994 | Stephens et al. | 607/15 |
| 5,292,341 A | 3/1994 | Snell | 607/30 |
| 5,311,874 A | 5/1994 | Baumann et al. | 128/705 |
| 5,312,452 A | 5/1994 | Salo | 607/17 |
| 5,331,966 A | 7/1994 | Bennett et al. | 128/696 |
| 5,334,220 A | 8/1994 | Sholder | 607/9 |
| 5,350,409 A | 9/1994 | Stoop et al. | 607/17 |
| 5,356,425 A | 10/1994 | Bardy et al. | 607/14 |
| 5,360,437 A | 11/1994 | Thompson | 607/30 |
| 5,365,932 A | 11/1994 | Greenhut | 128/696 |
| 5,372,607 A | 12/1994 | Stone et al. | 607/30 |
| 5,379,776 A | 1/1995 | Murphy et al. | 128/705 |
| 5,383,910 A | 1/1995 | den Dulk | 607/14 |
| 5,387,229 A | 2/1995 | Poore | 607/18 |
| 5,391,189 A | 2/1995 | van Krieken et al. | 607/17 |
| 5,395,373 A | 3/1995 | Ayers | 607/8 |
| 5,395,397 A | 3/1995 | Lindgren et al. | 607/9 |
| 5,400,796 A | 3/1995 | Wecke | 128/705 |
| 5,411,524 A | 5/1995 | Rahul | 607/4 |
| 5,411,531 A | 5/1995 | Hill et al. | 607/14 |
| 5,417,714 A | 5/1995 | Levine et al. | 607/9 |
| 5,423,869 A | 6/1995 | Poore et al. | 607/18 |
| 5,431,691 A | 7/1995 | Snell et al. | 607/27 |
| 5,437,285 A | 8/1995 | Verrier et al. | 128/702 |
| 5,462,060 A | 10/1995 | Jacobson et al. | 128/702 |
| 5,474,574 A | 12/1995 | Payne et al. | 607/7 |
| 5,480,413 A | 1/1996 | Greenhut et al. | 607/14 |
| 5,486,198 A | 1/1996 | Ayers et al. | 607/5 |
| 5,487,752 A | 1/1996 | Salo et al. | 607/17 |
| 5,507,782 A | 4/1996 | Kieval et al. | 607/9 |
| 5,507,784 A | 4/1996 | Hill et al. | 607/14 |
| 5,514,163 A | 5/1996 | Markowitz et al. | 607/9 |
| 5,522,850 A | 6/1996 | Yomtov et al. | 607/5 |
| 5,522,859 A | 6/1996 | Stroebel et al. | 607/19 |
| 5,523,942 A | 6/1996 | Tyler et al. | 364/401 |
| 5,527,347 A | 6/1996 | Shelton et al. | 607/9 |
| 5,534,016 A | 7/1996 | Boute | 607/9 |
| 5,540,232 A | 7/1996 | Laney et al. | 128/697 |
| 5,540,727 A | 7/1996 | Tockman et al. | 607/18 |
| 5,545,182 A | 8/1996 | Stotts et al. | 607/5 |
| 5,545,186 A | 8/1996 | Olson et al. | 607/14 |
| 5,549,649 A | 8/1996 | Florio et al. | 607/15 |
| 5,549,654 A | 8/1996 | Powell | 607/32 |
| 5,554,174 A | 9/1996 | Causey, III | 607/5 |
| 5,560,369 A | 10/1996 | McClure et al. | 128/704 |
| 5,560,370 A | 10/1996 | Verrier et al. | 128/705 |
| 5,584,864 A | 12/1996 | White | 607/5 |
| 5,584,867 A | 12/1996 | Limousin et al. | 607/9 |
| 5,591,215 A | 1/1997 | Greenhut et al. | 607/14 |
| 5,605,159 A | 2/1997 | Smith et al. | 128/702 |
| 5,607,460 A | 3/1997 | Kroll et al. | 607/30 |
| 5,613,495 A | 3/1997 | Mills et al. | 128/696 |
| 5,620,471 A | 4/1997 | Duncan | 607/14 |
| 5,620,473 A | 4/1997 | Poore | 607/27 |
| 5,622,178 A | 4/1997 | Gilham | 128/696 |
| 5,626,620 A | 5/1997 | Kieval et al. | 607/9 |
| 5,626,622 A | 5/1997 | Cooper | 607/18 |
| 5,626,623 A | 5/1997 | Kieval et al. | 607/23 |
| 5,632,267 A | 5/1997 | Hognelid et al. | 607/5 |
| 5,674,250 A | 10/1997 | de Coriolis et al. | 607/7 |
| 5,674,251 A | 10/1997 | Combs et al. | 607/4 |
| 5,674,255 A | 10/1997 | Walmsley et al. | 607/14 |
| 5,676,153 A | 10/1997 | Smith et al. | 128/702 |
| 5,683,429 A | 11/1997 | Mehra | 602/14 |
| 5,690,689 A | 11/1997 | Sholder | 607/24 |
| 5,700,283 A | 12/1997 | Salo | 607/17 |
| 5,702,424 A | 12/1997 | Legay et al. | |
| 5,713,929 A | 2/1998 | Hess et al. | 607/14 |
| 5,713,930 A | 2/1998 | van der Veen et al. | 607/25 |
| 5,713,932 A | 2/1998 | Gillberg et al. | 607/27 |
| 5,716,382 A | 2/1998 | Snell | 607/30 |
| 5,716,383 A | 2/1998 | Kieval et al. | 607/9 |
| 5,716,384 A | 2/1998 | Snell | 607/30 |
| 5,718,235 A | 2/1998 | Golosarsky et al. | 128/708 |
| 5,724,985 A | 3/1998 | Snell et al. | 128/697 |
| 5,725,559 A | 3/1998 | Alt et al. | 607/5 |
| 5,725,561 A | 3/1998 | Stroebel et al. | 607/9 |
| 5,730,141 A | 3/1998 | Fain et al. | 128/705 |
| 5,730,142 A | 3/1998 | Sun et al. | 128/705 |
| 5,738,096 A | 4/1998 | Ben-Haim | 128/653.1 |
| 5,741,304 A | 4/1998 | Patwardhan et al. | 607/5 |
| 5,741,308 A | 4/1998 | Sholder | 607/9 |
| 5,749,901 A | 5/1998 | Bush et al. | 607/5 |
| 5,749,906 A | 5/1998 | Kieval et al. | 607/9 |
| 5,755,736 A | 5/1998 | Gillberg et al. | 607/4 |
| 5,755,737 A | 5/1998 | Prieve et al. | 607/4 |
| 5,755,739 A | 5/1998 | Sun et al. | 607/14 |
| 5,755,740 A | 5/1998 | Nappholz | 607/18 |
| 5,759,196 A | 6/1998 | Hess et al. | 607/14 |
| 5,776,164 A | 7/1998 | Ripart | 607/5 |
| 5,776,167 A | 7/1998 | Levine et al. | 607/9 |
| 5,782,887 A | 7/1998 | van Krieken et al. | 607/25 |
| 5,788,717 A | 8/1998 | Mann et al. | 607/14 |
| 5,792,193 A | 8/1998 | Stoop | 607/14 |
| 5,800,464 A | 9/1998 | Kieval | 607/9 |
| 5,800,471 A | 9/1998 | Baumann | 607/25 |
| 5,814,077 A | 9/1998 | Sholder et al. | 607/9 |
| 5,814,081 A | 9/1998 | Ayers et al. | 607/5 |
| 5,814,085 A | 9/1998 | Hill | 607/14 |
| 5,836,975 A | 11/1998 | DeGroot | 607/5 |
| 5,836,987 A | 11/1998 | Baumann et al. | 607/17 |
| 5,840,079 A | 11/1998 | Warman et al. | 607/4 |
| 5,842,997 A | 12/1998 | Verrier et al. | 600/518 |
| 5,846,263 A | 12/1998 | Peterson et al. | 607/14 |
| 5,853,426 A | 12/1998 | Shieh | 607/5 |
| 5,855,593 A | 1/1999 | Olson et al. | 607/9 |
| 5,861,007 A | 1/1999 | Hess et al. | 607/9 |
| 5,865,838 A | 2/1999 | Obel et al. | 607/5 |
| 5,873,895 A | 2/1999 | Sholder et al. | 607/9 |
| 5,873,897 A | 2/1999 | Armstrong et al. | 607/14 |
| 5,891,178 A | 4/1999 | Mann et al. | 607/27 |
| 5,893,882 A | 4/1999 | Peterson et al. | 607/14 |
| 5,897,575 A | 4/1999 | Wickham | 607/4 |
| 5,902,324 A | 5/1999 | Thompson et al. | 607/9 |
| 5,928,271 A | 7/1999 | Hess et al. | 607/14 |
| 5,931,857 A | 8/1999 | Prieve et al. | 607/14 |
| 5,935,081 A | 8/1999 | Kadhiresan | 600/513 |
| 5,944,744 A | 8/1999 | Paul et al. | 607/9 |
| 5,951,592 A | 9/1999 | Murphy | 607/4 |
| 5,968,079 A | 10/1999 | Warman et al. | 607/5 |
| 5,974,341 A | 10/1999 | Er et al. | 607/31 |
| 5,978,707 A | 11/1999 | Krig et al. | 607/14 |
| 5,978,710 A | 11/1999 | Prutchi et al. | 607/17 |

| | | | |
|---|---|---|---|
| 5,983,138 A | 11/1999 | Kramer | 607/9 |
| 5,987,354 A | 11/1999 | Cooper et al. | 607/5 |
| 5,987,356 A | 11/1999 | DeGroot | 607/5 |
| 5,991,656 A | 11/1999 | Olson et al. | 607/4 |
| 5,991,657 A | 11/1999 | Kim | 607/5 |
| 5,991,662 A | 11/1999 | Kim et al. | 607/27 |
| 5,999,850 A | 12/1999 | Dawson et al. | 607/4 |
| 6,026,320 A | 2/2000 | Carlson et al. | 600/510 |
| 6,041,251 A | 3/2000 | Kim et al. | 600/518 |
| 6,044,298 A | 3/2000 | Salo et al. | 607/17 |
| 6,047,210 A | 4/2000 | Kim et al. | 607/4 |
| 6,049,735 A | 4/2000 | Hartley et al. | 607/9 |
| 6,052,617 A | 4/2000 | Kim | 600/518 |
| 6,052,620 A | 4/2000 | Gillberg et al. | 607/4 |
| 6,058,328 A | 5/2000 | Levine et al. | 607/14 |
| 6,081,745 A | 6/2000 | Mehra | 607/4 |
| 6,081,746 A | 6/2000 | Pendekanti et al. | 607/5 |
| 6,081,747 A | 6/2000 | Levine et al. | 607/9 |
| 6,081,748 A | 6/2000 | Struble et al. | 607/9 |
| RE36,765 E | 7/2000 | Mehra | 607/4 |
| 6,085,116 A | 7/2000 | Pendekanti et al. | 607/5 |
| 6,088,618 A | 7/2000 | Kerver | 607/30 |
| 6,091,988 A | 7/2000 | Warman et al. | 607/5 |
| 6,096,064 A | 8/2000 | Routh | 607/9 |
| 6,122,545 A | 9/2000 | Struble et al. | 607/9 |
| 6,128,529 A | 10/2000 | Elser | 607/4 |
| 6,129,745 A | 10/2000 | Sun et al. | 607/27 |
| 6,151,524 A | 11/2000 | Krig et al. | 607/14 |
| 6,223,072 B1 | 4/2001 | Mika et al. | 600/510 |
| 6,246,909 B1 | 6/2001 | Ekwall | 607/9 |
| 6,249,699 B1 | 6/2001 | Kim | 607/4 |
| 6,256,534 B1 | 7/2001 | Dahl | 607/5 |
| 6,263,242 B1 | 7/2001 | Mika et al. | 607/9 |
| 6,266,554 B1 | 7/2001 | Hsu et al. | 600/515 |
| 6,272,380 B1 | 8/2001 | Warman et al. | 607/5 |
| 6,285,907 B1 | 9/2001 | Kramer et al. | 607/9 |
| 6,292,693 B1 | 9/2001 | Darvish et al. | |
| 6,317,632 B1 | 11/2001 | Krig et al. | 607/14 |
| 6,351,669 B1 | 2/2002 | Hartley et al. | |
| 6,353,759 B1 | 3/2002 | Hartley et al. | 607/9 |
| 6,353,761 B1 | 3/2002 | Conley et al. | 607/28 |
| 6,408,209 B1 | 6/2002 | Bouhour et al. | 607/19 |
| 6,411,847 B1 | 6/2002 | Mower | 607/9 |
| 6,411,848 B1 | 6/2002 | Kramer et al. | 607/9 |
| 6,424,865 B1 | 7/2002 | Ding | 607/9 |
| 6,430,438 B1 | 8/2002 | Chen et al. | 607/5 |
| 6,430,439 B1 * | 8/2002 | Wentkowski et al. | 607/9 |
| 6,434,424 B1 | 8/2002 | Igel et al. | 607/9 |
| 6,438,410 B1 | 8/2002 | Hsu et al. | 600/516 |
| 6,438,421 B1 * | 8/2002 | Stahmann et al. | 607/9 |
| 6,501,987 B1 | 12/2002 | Lovett et al. | 607/9 |
| 6,501,988 B1 | 12/2002 | Kramer et al. | 607/9 |
| 6,512,951 B1 | 1/2003 | Marcovecchio et al. | 607/5 |
| 6,522,925 B1 | 2/2003 | Gilkerson et al. | |
| RE38,119 E | 5/2003 | Mower | 607/9 |
| 6,687,541 B1 | 2/2004 | Marcovecchio et al. | |
| 6,763,267 B1 | 7/2004 | Ding | |
| 6,847,842 B1 | 1/2005 | Rodenhiser et al. | |
| 2002/0062139 A1 | 5/2002 | Ding | |
| 2002/0082509 A1 | 6/2002 | Vanderlinde et al. | |
| 2002/0082660 A1 | 6/2002 | Stahmann et al. | |
| 2002/0087198 A1 | 7/2002 | Kramer et al. | |
| 2002/0091415 A1 | 7/2002 | Lovett et al. | |
| 2002/0120298 A1 | 8/2002 | Kramer et al. | |
| 2003/0004551 A1 | 1/2003 | Chen et al. | |
| 2003/0069610 A1 | 4/2003 | Kramer et al. | |
| 2003/0078630 A1 | 4/2003 | Lovett et al. | |
| 2003/0105491 A1 | 6/2003 | Gilkerson et al. | |
| 2003/0233131 A1 | 12/2003 | Kramer et al. | |
| 2004/0010295 A1 | 1/2004 | Kramer et al. | |
| 2004/0172076 A1 | 9/2004 | Stahmann et al. | |
| 2004/0215259 A1 | 10/2004 | Krig et al. | |
| 2004/0243188 A1 | 12/2004 | Vanderlinde et al. | |
| 2005/0038480 A1 | 2/2005 | Ding | |

FOREIGN PATENT DOCUMENTS

| | | |
|---|---|---|
| EP | 0360412 | 3/1990 |
| EP | 0401962 | 12/1990 |
| EP | 0597459 | 5/1994 |
| EP | 0617980 | 10/1994 |
| EP | 0748638 | 12/1996 |
| WO | WO-93/02746 | 2/1993 |
| WO | WO-95/09029 | 4/1995 |
| WO | WO-97/11745 | 4/1997 |
| WO | WO-98/48891 | 11/1998 |
| WO | WO-00/71200 | 11/2000 |
| WO | WO-00/71202 | 11/2000 |
| WO | WO-00/71203 | 11/2000 |
| WO | WO-0071200 A1 | 11/2000 |
| WO | WO-0071202 A1 | 11/2000 |
| WO | WO-0071203 A1 | 11/2000 |

OTHER PUBLICATIONS

Guidant, "CONTAK TR CHFD Model 1241", *System Guide*, Congestive Heart Failure Device, (1999), 1-191.

Krig, D. B., et al., "Method and Apparatus for Treating Irregular Ventricular Contractions Such as During Atrial Arrhythmia", U.S. Appl. No. 09/316,515, filed May 21, 1999, 57 Pages.

Lovett, Eric, "Cardiac Pacing System for Prevention of Ventricular Fibrillation and Ventricular Tachycardia Episode", U.S. Serial No. 09/569,295, filed May 13, 2000, 71 pgs.

Medtronic, "INSYNC III Device Model 8042", *Device Programming Guide*, INSYNC III Device Model 8042, Vision Programmer Software Model 9981, (2002), 1-260.

Medtronic, "INSYNC III Device Model 8042", *Device Reference Guide*, INSYNC III Device Model 8042, Vision Programmer Software Model 9981, (2002), 1-252.

St. Jude Medical, "Atlas + HF Models V-343, V-341", *User's Manual*, Implantable Cardioverter-Defibrillator, (Sep. 2003), 1-30.

St. Jude Medical, "Epic HF Model V-339", *User's Manual*, Implantable Cardioverter-Defibrillator, (Jul. 2002), 1-26.

St. Jude Medical, "Model 3510 Programmer with Model 3307 Software", *Reference Manual*, For Atlas, Atlas+, Epic, Epic+, Photon u and Photon Implantable Cardioverter/Defibrillators, (Sep. 2003), 1-314.

Buhr, Trina A., et al., "Novel Pacemaker Algorithm Diminishes Short-Coupled Ventricular Beats In Atrial Fibrillation", *PACE*, vol. 24, Part II, (Apr. 2001),729.

Greenhut, S., et al., "Effectiveness of a Ventricular Rate Stabilization Algorithm During Atrial Fibrillation in Dogs", *Pace Abstract*, Abstract No. 60,(1996),1 p.

Lau, Chu-Pak, et al., "Efficacy of Ventricular Rate Stabilization by Right Ventricular Pacing During Atrial Fibrillation", *PACE*, vol. 21, (Mar. 1998),542-548.

Wittkampf, Fred H., et al., "Effect of Right Ventricular Pacing on Ventricular Rhythm During Atrial Fibrillation", *JACC*, vol. 11, No. 3, (Mar. 1988),539-545.

Wittkampf, F.H.M. , et al., "Rate Stabilization by Right Ventricular Pacing in Patients with Atrial Fibrillation", *Pace*, vol. 9, Part II, (Nov.-Dec. 1986),1147-1153.

*Metrix Model 3020 Implantable Atrial Defibrillator*, Physician's Manual, InControl, Inc. Redmond, WA,(1998),pp. 4-24-4-27.

"French CNH Equipment Approvals", *Clinica*, 417, p. 9, (Sep. 5, 1990),3 pages.

"Pacemaker System Guide for Pulsar Max II; Mulitprogrammable Pacemakers", Product brochure published by Guidant Corporation,(Apr. 18, 1999),pg. 6—48 and 6—49.

"Pacemaker System Guide for Pulsar Max II; Multiprogrammable Pacemakers", Product brochure published by Guidant Corporation,(1999),pg. 6-39-6-51.

"Rate-Adaptive Devices Impact Pacemaker Market", *Clinica*, 467, p. 16, (Sep. 11, 1991),6 pages.

"Vitatron Medical Harmony Automatic Dual Chamber Pacemaker Product Information and Programming Guide", Product Brochure published by Vitatron Medical,(Date Unknown),22 pgs.

Ayers, Gregory M., et al., "Ventricular Proarrhythmic Effects of Ventricular Cycle Length and Shock Strength in a Sheep Model of Transvenous Atrial Defibrillation", *Circulation*, 89 (1), (Jan. 1994),pp. 413-422.

Blommaert, D., et al., "Effective Prevention of Atrial Fibrillation by Continuous Atrial Overdrive Pacing After Coronary Artery Bypass Surgery", *JACC*, vol. 35, No. 6, (May 2000),pp. 1411-1415.

Campbell, R. M., et al., "Atrial Overdrive Pacing for Conversion of Atrial Flutter in Children", *Pediatrics*, vol. 75, No. 4, (Apr. 1985),pp. 730-736.

Duckers, H. J., et al., "Effective use of a novel rate-smoothing algorithm in atrial fibrillation by ventricular pacing", *European Heart Journal*, 18, (1997),pp.1951-1955.

Fahy, G. J., et al., "Pacing Strategies to Prevent Atrial Fibrillation", *Atrial Fibrillation*, 14 (4), (Nov. 1996),pp. 591-596.

Fromer, M. , et al., "Algorithm for the Prevention of Ventricular Tachycardia Onset: The Prevent Study", *The American Journal of Cardiology*, 83 (5B), (Mar. 11, 1999),pp. 45D-47D.

Garrigue, S. , et al., "Prevention of Atrial Arrhythmias during DDD Pacing by Atrial Overdrive", *PACE*, vol. 21, (Sep. 1998),pp. 1751-1759.

Heuer, H. , et al., "Dynamic Dual-Chamber Overdrive Pacing with an Implantable Pacemaker System: A New Method for Terminating Slow Ventricular Tachycardia", *Zeitschrift fur Kardiologie*, 75, German Translation by the Ralph McElroy Translation Company, Austin, TX,(1986),5 p.

Heuer, H. , et al., "Dynamische Zweikammer-Overdrive-Stimulation mit einem implantierbaren Schrittmachersystem als neue Methode zur Beendigung Langsamer ventrikularer Tachykardien", *Z Kardiol*; 75, Includes English translation (5 pgs.),(1986),pp. 673-675.

Jenkins, et al., "Diagnosis of Atrial Fibrillation Using Electrogram from Chronic Leads: Evaluation of Computer Algorithm", *PACE*, 11, (1988),pp. 622-631.

Jung, J. , et al., "Discrimination of Sinus Rhythm, Atrial Flutter, and Atrial Fibrillation Using Bipolar Endocardial Signals", *Journal of Cardiovascular Electrophysiology*, 9 (7), (Jul. 1998),pp. 689-695.

Mehra, R. , et al., "Prevention of Atrial Fibrillation/Flutter by Pacing Techniques", *Interventional Electrophysiology, Second Edition*, Chapter 34, Futura Publishing Company, Inc.,(1996),pp. 521-540.

Morris, et al., "Intracardiac Electrogram Transformation: Morphometric Implications for Implantable Devices", *Journal of Electrocardiology*, 29 Supplement, (1996),pp. 124-129.

Mower, Morton , U.S. Patent Office Patent Application Information Retrieval (PAIR) search results for U.S. Appl. No. 10/214,474, filed Aug. 8, 2002, entitled "Method and Apparatus for Treating Hemodynamic Disfunction", 3.

Murgatroyd, F. D., et al., "A New Pacing Algorithm for Overdrive Suppression of Atrial Fibrillation", *Pace*, vol. 17., (Nov. 1994, Part),pp. 1966-1973.

Schuller, et al., "Far Field R-Wave Sensing—An Old Problem Repeating", *PACE*, 19, Part II, NASPE Abstract No. 264,(1996),p. 631.

Seim, G. , et al., "Classification Atrial Flutter and Atrial Fibrillation Using an Atrial Dispersion Index (ADI)", *Guidant CRM Therapy Research Peer Review Report Revision 2.0*, (Jan. 6, 1999),27 p.

Stephany, et al., "Real-Time Estimation of Magnitude-Square Coherence for Use in Implantable Devices", *IEEE Computers in Cardiology*, (1992),pp. 375-378.

Sutton, R. , "Pacing in Atrial Arrhythmias", *PACE*, vol. 13, (Dec. 1990, Part),pp. 1823-1827.

Swiryn, S. , et al., "Detection of Atrial Fibrillation by Pacemakers and Antiarrhythmic Devices", *Nonpharmacological Management of Atrial Fibrillation*, Chapter 21, Futura Publishing Co, Inc. Armonk, NY,(1997),pp. 309-318.

Zhu, D. W., "Electrophysiology, Pacing and Arrhythmia", *Clin. Cardiol.*, vol. 19, (Sep. 1996),pp.737-742.

\* cited by examiner

APPARATUS AND METHOD FOR VENTRICULAR RATE REGULARIZATION

CROSS-REFERENCE TO RELATED APPLICATION(S)

This application is a continuation of U.S. application Ser. No. 09/751,431, filed on Dec. 29, 2000, now abandoned the specification of which is incorporated herein by reference.

This application is related to the following co-pending, commonly assigned patent application: "System Providing Ventricular Pacing and Biventricular Coordination," U.S. Ser. No. 09/316,588, filed on May 21, 1999, which disclosure is herein incorporated by reference in its entirety.

FIELD OF THE INVENTION

This invention pertains to cardiac pacemakers and methods for operating such devices. In particular, the invention relates to methods for employing pacing therapy to maintain hemodynamic stability.

BACKGROUND

Ventricular tachyarrhythmias, in which the ventricles beat more rapidly and irregularly than normal, can be due to a variety of etiologies. Certain patients, for example, are prone to premature ventricular contractions due to ectopic excitatory foci in the ventricular myocardium. Another cause of ventricular tachyarrhythmia is atrial fibrillation where the atria depolarize in a chaotic fashion with no effective pumping action. The intrinsic ventricular rhythm that occurs during an episode of atrial fibrillation is a result of the chaotically occurring depolarizations occurring in the atria being passed through the AV node to the ventricles. The intrinsic ventricular rate is thus governed by the cycle length of the atrial fibrillation and the refractory period of the AV node. Although the intrinsic ventricular rate is less than the atrial rate, due to the refractory period of the AV node, it is still rapid and irregular.

When the ventricles contract at irregular intervals, the contraction can occur prematurely before diastolic filling is complete which decreases the stroke volume for that contraction. This can be especially significant in, for example, congestive heart failure patients who are already hemodynamically compromised. Concomitant atrial fibrillation where the atria no longer act as effective priming pumps can also contribute to the problem. An irregular ventricular rate can thus depress cardiac output and cause such symptoms as dyspnea, fatigue, vertigo, and angina. An objective of the present invention is to use pacing therapy to maintain hemodynamic stability in the presence of an irregular intrinsic ventricular rhythm.

SUMMARY OF THE INVENTION

The present invention is a system and method for regularizing the ventricular rate by adjusting the lower rate limit of a pacemaker in accordance with changes in the measured intrinsic ventricular rate. By making the ventricular escape interval track a mean interval between intrinsic beats, less variability in the overall ventricular rhythm is allowed by the pacemaker. Ventricular rate regularization improves cardiac output when used with conventional bradycardia pacing. Ventricular rate regularization may also be used to improve the efficacy of ventricular resynchronization therapy and anti-tachyarrhythmia therapy.

DETAILED DESCRIPTION OF THE INVENTION

As will be described below, ventricular rate regularization may be advantageously applied together with a number of different cardiac rhythm management therapies. These include conventional bradycardia pacing, ventricular resynchronization therapy, and anti-tachyarrhythmia therapy.

1. System Description

Figure 1:
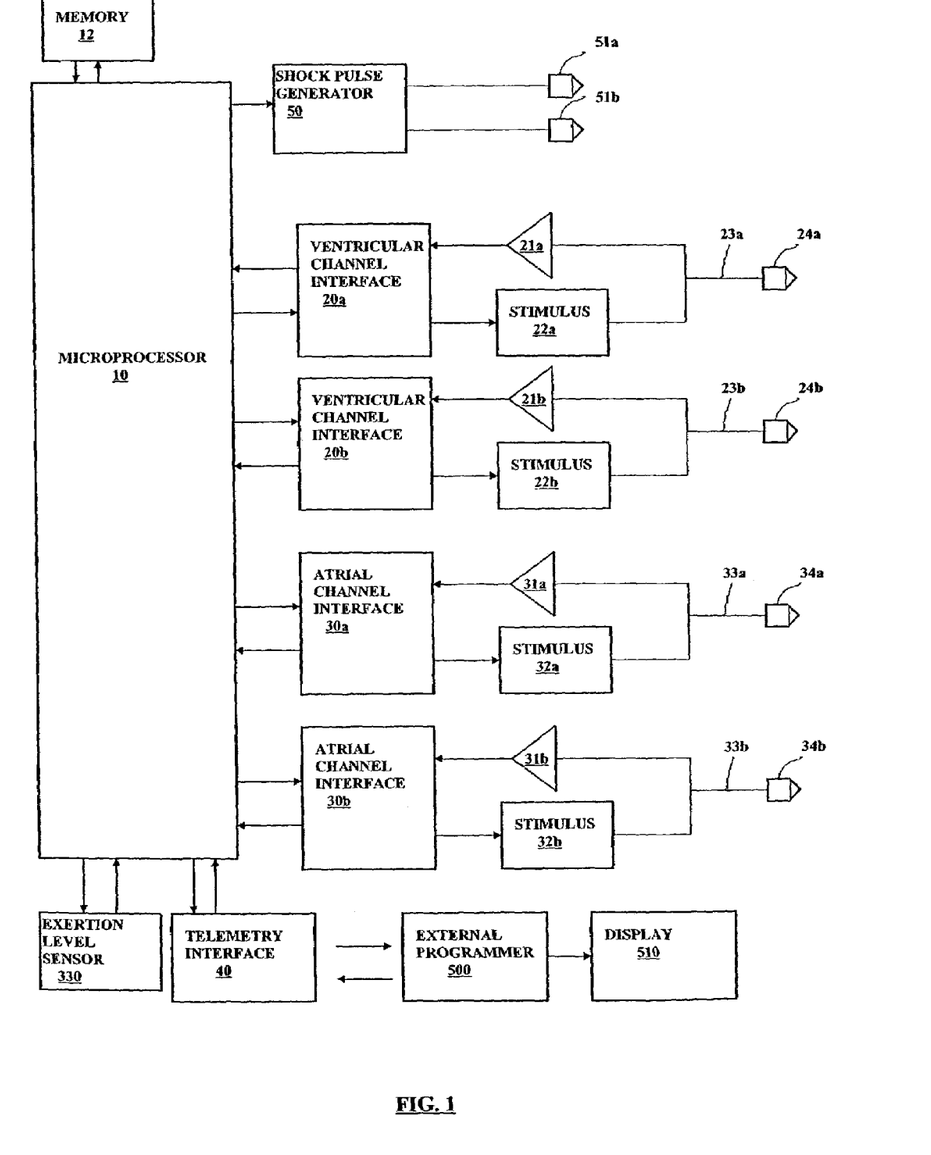
FIG. 1 is a system diagram of a microprocessor-based cardiac rhythm management device.

FIG. 1 shows a system diagram of a microprocessor-based cardiac rhythm management device suitable for delivering ventricular rate regularization therapy as well as various cardiac rhythm management therapies with which ventricular rate regularization can be advantageously combined. In the particular embodiments to be described below, a device incorporating the present invention may possess all of the components shown or only those necessary to perform the functions described.

The device in FIG. 1 is a pacemaker that is physically configured with sensing and pacing channels for both atria and both ventricles. The controller 10 of the device is a microprocessor which communicates with a memory 12 via a bidirectional data bus. The memory 12 typically comprises a ROM (read-only memory) for program storage and a RAM (random-access memory) for data storage. The pacemaker has atrial sensing and pacing channels comprising electrode 34a–b, leads 33a–b, sensing amplifiers 31a–b, pulse generators 32a–b, and atrial channel interfaces 30a–b which communicate bidirectionally with microprocessor 10. The device also has ventricular sensing and pacing channels for both ventricles comprising electrodes 24a–b, leads 23a–b, sensing amplifiers 21a–b, pulse generators 22a–b, and ventricular channel interfaces 20a–b. In the figure, "a" designates one ventricular or atrial channel and "b" designates the channel for the contralateral chamber. In this embodiment, a single electrode is used for sensing and pacing in each channel, known as a unipolar lead. Other embodiments may employ bipolar leads which include two electrodes for outputting a pacing pulse and/or sensing intrinsic activity. The channel interfaces 20a–b and 30a–b include analog-to-digital converters for digitizing sensing signal inputs from the sensing amplifiers and registers which can be written to by the microprocessor in order to output pacing pulses, change the pacing pulse amplitude, and adjust the gain and threshold values for the sensing amplifiers. An exertion level sensor 330 (e.g., an accelerometer or a minute ventilation sensor) enables the controller to adapt the pacing rate in accordance with changes in the patient's physical activity. A telemetry interface 40 is also provided for communicating with an external programmer 500 which has an associated display 510.

The device of FIG. 1 is also configured to deliver anti-tachyarrhythmia therapy by anti-tachycardia pacing and/or cardioversion/defibrillation. Tachyarrhythmias are abnormal heart rhythms characterized by a rapid heart rate. Examples of tachyarrhythmias include supraventricular tachycardias such as sinus tachycardia, atrial tachycardia, and atrial fibrillation (AF), and ventricular tachyarrhythmias such as ventricular tachycardia (VT) and ventricular fibrillation (VF). Both ventricular tachycardia and ventricular fibrillation are hemodynamically compromising, and both can be life-threatening. Atrial fibrillation is not immediately life threatening, but since atrial contraction is lost, the ventricles are not filled to capacity before systole which reduces cardiac output. If atrial fibrillation remains untreated for long periods of time, it can also cause blood to clot in the left atrium, possibly forming emboli and placing patients at risk for stroke.

Cardioversion (an electrical shock delivered to the heart synchronously with an intrinsic depolarization) and defibrillation (an electrical shock delivered without such synchronization) can be used to terminate most tachyarrhythmias, including AF, VT, and VF. As used herein, the term defibrillation should be taken to mean an electrical shock delivered either synchronously or not in order to terminate a fibrillation. In electrical defibrillation, a current depolarizes a critical mass of myocardial cells so that the remaining myocardial cells are not sufficient to sustain the fibrillation. The electric shock may thus terminate the tachyarrhythmia by depolarizing excitable myocardium, which thereby prolongs refractoriness, interrupts reentrant circuits, and discharges excitatory foci.

The device in FIG. 1 has a cardioversion/defibrillation functionality as implemented by a shock pulse generator 50 interfaced to the microprocessor for delivering shock pulses via a pair of shock electrodes 51a and 51b placed in proximity to regions of the heart. The device may have one such shock pulse generator and shock electrode pair for delivering defibrillation shocks to either the atria or the ventricles or may be capable of delivering shocks to both chambers. The sensing channels are used to both control pacing and for measuring heart rate in order to detect tachyarrhythmias such as fibrillation. The device detects an atrial or ventricular tachyarrhythmia by measuring the atrial or ventricular rate, respectively, as well as possibly performing other processing on data received from the sensing channels.

2. Bradycardia Pacing Modes

Bradycardia pacing modes refer to pacing algorithms used to pace the atria and/or ventricles when the intrinsic ventricular rate is inadequate either due to AV conduction blocks or sinus node dysfunction. Such modes may either be single-chamber pacing, where either an atrium or a ventricle is paced, or dual-chamber pacing in which both an atrium and a ventricle are paced. The modes are generally designated by a letter code of three positions where each letter in the code refers to a specific function of the pacemaker. The first letter refers to which heart chambers are paced and which may be an A (for atrium), a V (for ventricle), D (for both chambers), or O (for none). The second letter refers to which chambers are sensed by the pacemaker's sensing channels and uses the same letter designations as used for pacing. The third letter refers to the pacemaker's response to a sensed P wave from the atrium or an R wave from the ventricle and may be an I (for inhibited), T (for triggered), D (for dual in which both triggering and inhibition are used), and O (for no response). Modem pacemakers are typically programmable so that they can operate in any mode which the physical configuration of the device will allow. Additional sensing of physiological data allows some pacemakers to change the rate at which they pace the heart in accordance with some parameter correlated to metabolic demand. Such pacemakers are called rate-adaptive pacemakers and are designated by a fourth letter added to the three-letter code, R.

Pacemakers can enforce a minimum heart rate either asynchronously or synchronously. In asynchronous pacing, the heart is paced at a fixed rate irrespective of intrinsic cardiac activity. There is thus a risk with asynchronous pacing that a pacing pulse will be delivered coincident with an intrinsic beat and during the heart's vulnerable period which may cause fibrillation. Most pacemakers for treating bradycardia today are therefore programmed to operate synchronously in a so-called demand mode where sensed cardiac events occurring within a defined interval either trigger or inhibit a pacing pulse. Inhibited demand pacing modes utilize escape intervals to control pacing in accordance with sensed intrinsic activity. In an inhibited demand mode, a pacing pulse is delivered to a heart chamber during a cardiac cycle only after expiration of a defined escape interval during which no intrinsic beat by the chamber is detected. If an intrinsic beat occurs during this interval, the heart is thus allowed to "escape" from pacing by the pacemaker. Such an escape interval can be defined for each paced chamber. For example, a ventricular escape interval can be defined between ventricular events so as to be restarted with each ventricular sense or pace. The inverse of this escape interval is the minimum rate at which the pacemaker will allow the ventricles to beat, sometimes referred to as the lower rate limit (LRL).

In atrial tracking pacemakers (i.e., VDD or DDD mode), another ventricular escape interval is defined between atrial and ventricular events, referred to as the atrio-ventricular interval (AVI). The atrio-ventricular interval is triggered by an atrial sense or pace and stopped by a ventricular sense or pace. A ventricular pace is delivered upon expiration of the atrio-ventricular interval if no ventricular sense occurs before. Atrial-tracking ventricular pacing attempts to maintain the atrio-ventricular synchrony occurring with physiological beats whereby atrial contractions augment diastolic filling of the ventricles. If a patient has a physiologically normal atrial rhythm, atrial-tracking pacing also allows the ventricular pacing rate to be responsive to the metabolic needs of the body.

A pacemaker can also be configured to pace the atria on an inhibited demand basis. An atrial escape interval is then defined as the maximum time interval in which an atrial sense must be detected after a ventricular sense or pace before an atrial pace will be delivered. When atrial inhibited demand pacing is combined with atrial-triggered ventricular demand pacing (i.e., DDD mode), the lower rate interval is then the sum of the atrial escape interval and the atrio-ventricular interval.

Another type of synchronous pacing is atrial-triggered or ventricular-triggered pacing. In this mode, an atrium or ventricle is paced immediately after an intrinsic beat is detected in the respective chamber. Triggered pacing of a heart chamber is normally combined with inhibited demand pacing so that a pace is also delivered upon expiration of an escape interval in which no intrinsic beat occurs. Such triggered pacing may be employed as a safer alternative to asynchronous pacing when, due to far-field sensing of electromagnetic interference from external sources or skeletal muscle, false inhibition of pacing pulses is a problem. If a sense in the chamber's sensing channel is an actual depolarization and not a far-field sense, the triggered pace is delivered during the chamber's physiological refractory period and is of no consequence.

Finally, rate-adaptive algorithms may be used in conjunction with bradycardia pacing modes. Rate-adaptive pacemakers modulate the ventricular and/or atrial escape intervals based upon measurements corresponding to physical activity. Such pacemakers are applicable to situations in which atrial tracking modes cannot be use. In a rate-adaptive pacemaker operating in a ventricular pacing mode, the LRL is adjusted in accordance with exertion level measurements such as from an accelerometer or minute ventilation sensor in order for the heart rate to more nearly match metabolic demand. The adjusted LRL is then termed the sensor-indicated rate.

3. Ventricular Rate Regularization

Ventricular rate regularization (VRR) is a ventricular pacing mode in which the LRL of the pacemaker is dynamically adjusted in accordance with a detected intrinsic ventricular rate. When a pacemaker is operating in a ventricular demand pacing mode (e.g., VVI), intrinsic ventricular beats occur when the instantaneous intrinsic rate rises above the LRL of the pacemaker. Thus, paces can be interspersed with intrinsic beats, and the overall ventricular rhythm as a result of both paces and intrinsic beats is determined by the LRL and the mean value and variability of the intrinsic ventricular rate. VRR regularizes the overall ventricular rhythm by adjusting the LRL of the pacemaker in accordance with changes in the measured intrinsic rate.

The intrinsic ventricular rate is the rate at which intrinsic ventricular beats occur and can be defined both instantaneously and as being at some mean value with a certain variability about that mean. The instantaneous intrinsic rate can be determined by measuring an R—R interval, where an R—R interval is the time between a present ventricular sense (i.e., an R-wave or intrinsic ventricular depolarization) and the preceding ventricular sense or ventricular pace, with the instantaneous rate being the reciprocal of the measured interval. The mean intrinsic rate can be determined by averaging the instantaneous R—R intervals over a period of time. The LRL of a pacemaker is initially set to a programmed base value and defines the ventricular escape interval, which is the maximum time between ventricular beats allowed by the pacemaker and is the reciprocal of the LRL. At any particular mean intrinsic rate above the LRL, a ventricular pace is delivered only when, due to the variability in the intrinsic rate, an R—R interval would be longer than the ventricular escape interval were it allowed to occur. As the mean intrinsic ventricular rate increases above the LRL, fewer paces are delivered and more variability in the overall ventricular rhythm is allowed. The VRR pacing mode counteracts this by increasing the LRL as the mean intrinsic ventricular rate increases to thereby increase the frequency of paced beats which decreases the incidence of long intrinsic R—R intervals and thus lessens the variability in the overall ventricular rate. The VRR mode then decreases the LRL toward its base value as the number of paces delivered increases due to a decrease in either the mean intrinsic ventricular rate or its variability. The LRL adjusted in this manner is also referred to herein as the VRR-indicated rate.

Figure 2:
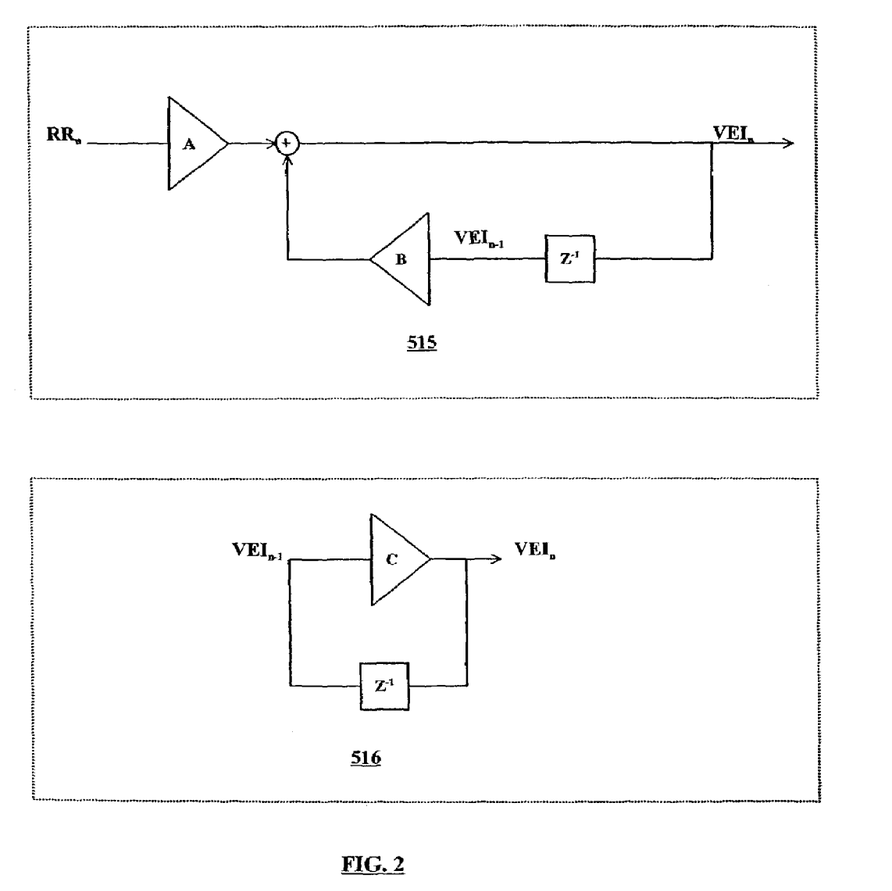
FIG. 2 shows an exemplary filter implementation of a ventricular rate regularization system.

In one embodiment of VRR, the LRL is adjusted to increase toward a programmed maximum value by measuring an R—R interval when a ventricular sense occurs and then computing an updated ventricular escape interval based upon the measured R—R interval. When a ventricular pace is delivered, on the other hand, the LRL is made to decay toward the programmed base value. FIG. 2 shows an exemplary implementation of a VRR system made up of a pair of filters 515 and 516 which may be implemented as software executed by the controller 10 and/or with discrete components. Filter 515 is employed to compute the updated ventricular escape interval when a ventricular sense occurs, and filter 516 is used when a ventricular pace is delivered.

When a ventricular sense occurs, the measured R—R interval is input to a recursive digital filter 515 whose output is the updated ventricular escape interval. The filter 515 multiplies the measured R—R interval by a filter coefficient A and then adds the result to the previous value of the output (i.e., the present ventricular escape interval) multiplied by a filter coefficient B. The operation of the filter is thus described by $VEI_n = A(RR_n) + B(VEI_{n-1})$, where A and B are selected coefficients, $RR_n$ is the most recent R—R interval duration, and $VEI_{n-1}$ is the previous value of the ventricular escape interval. A useful way to conceptualize the filter 515 is to decompose the coefficients A and B into a scaling factor a and a weighting coefficient w such that $A = a \cdot w$ and $B = (1-w)$, where w is between 0 and 1. Viewed this way, the filter is seen as computing a weighted average of the present R—R interval multiplied by the scaling factor a and the present ventricular escape interval. The filter thus causes the value of the ventricular escape interval to move toward the present R—R interval multiplied by the scaling factor at a rate determined by the weighting coefficient. This corresponds to the filter moving the pacemaker's LRL toward a fraction 1/a of the instantaneous intrinsic ventricular rate, up to a maximum pacing rate MPR, as determined by the measured R—R interval. If a ventricular sense has occurred, the current LRL is necessarily less than the measured instantaneous intrinsic ventricular rate. If it is also less than 1/a of the intrinsic rate, the LRL is increased by the filter up to a value that is 1/a of the intrinsic rate (as limited by the MPR) to result in more pacing and less variability in the overall ventricular rhythm.

When a ventricular pace is delivered due to expiration of the ventricular escape interval without a ventricular sense, filter 516 multiplies the present ventricular escape interval by a filter coefficient C so that $VEI_n = C(VEI_{n-1})$. To provide stable operation, the coefficient C must be set to a value greater than 1. Filter 516 then causes the ventricular escape interval to increase in an exponential manner with each pace as successive values of the escape interval are input to the filter up to a value corresponding to the base LRL.

The updating of the ventricular escape interval may be performed in various ways including on a beat-to-beat basis, at periodic intervals, or with averages of successive R—R intervals. In a presently preferred embodiment, however, the updating is performed on a beat-to-beat basis with each ventricular sense or pace causing adjustment of the LRL by filter 515 or 516, respectively. The two filters operating together thus cause the LRL to move closer to 1/a of the measured intrinsic rate (up to the MPR) after a ventricular sense and to decay toward the base LRL value after a ventricular pace.

The coefficients a and w (or A and B) and C are selected by the user and may be made programmable so that the behavior of the system can be adjusted to produce the clinically best result in an individual patient. For example, as the scaling factor a is made greater than 1, the filter 515 causes the LRL to move toward a smaller fraction 1/a of the detected intrinsic rate which allows more intrinsic beats to occur and greater variability in the overall rhythm. As a is decreased back toward 1, the filter 515 tends to move the LRL of the pacemaker toward a larger fraction of the detected instantaneous intrinsic rate, thus increasing the amount of pacing and decreasing the amount of variability allowed in the overall ventricular rhythm. If a is made smaller than 1, the LRL is moved toward a rate higher than the intrinsic rate, further increasing the amount of pacing to a point where most of the ventricular rhythm is made up of paced beats. The larger the weighting factor w, the faster the LRL is moved to the specified fraction of the intrinsic rate, making the system more responsive to increases in the variability of the intrinsic rhythm. The larger the decay coefficient C, the more rapidly will filter 516 cause the LRL to decrease toward its programmed base value when ventricular paces are delivered due to no ventricular senses being detected within the ventricular escape interval. The controller limits the updated ventricular escape interval as a result of the operations of filters 515 and 516 to minimum and maximum values in accordance with the programmed maximum pacing rate MPR and base lower rate limit LRL, respectively.

As noted, the coefficients of filters 515 and 516 can be made programmable by the user, such as by using a remote programmer. In another embodiment, the user selects a desired performance parameter (e.g., desired degree of rate regularization, desired amount of pacing, desired decay rate, etc.) from a corresponding range of possible values. The appropriate combinations of coefficients for filters 515 and 516 are then automatically selected to provide filter settings that correspond to the selected user-programmed performance parameter. The filter coefficients can also be made functions of other parameters, such as the measured R—R interval and current LRL setting, and dynamically adjusted.

The VRR system in this embodiment uses the programmed base LRL of the pacemaker as the lower limit to which the LRL is permitted to decay when no ventricular senses are detected. The base LRL can be changed periodically by the user with an external programmer, and certain pacemakers also have the capability of dynamically adjusting the LRL in order to adapt to exercise. In such rate-adaptive pacemakers, the LRL is adjusted in accordance with exertion level measurements such as from an accelerometer or minute ventilation sensor in order for the heart rate to more nearly match metabolic demand. The adjusted LRL is then termed the sensor-indicated rate. If a rate-adaptive pacemaker is operated in a VRR mode, the sensor-indicated rate can simply be regarded by the pacemaker as the base LRL. The lower limit for the VRR-indicated rate is then the sensor-indicated rate rather than the programmed base LRL.

VRR can thus be employed to modify conventional bradycardia pacing in order to improve the deleterious hemodynamic effects brought about by an irregular intrinsic ventricular rhythm. As will be described below, VRR also has some special advantages when used in conjunction with other cardiac rhythm management therapies.

4. Ventricular Rate Regularization with Cardiac Resynchronization Therapy

Heart failure is clinical syndrome in which an abnormality of cardiac function causes cardiac output to fall below a level adequate to meet the metabolic demand of peripheral tissues and is usually referred to as congestive heart failure (CHF) due to the accompanying venous and pulmonary congestion. CHF can be due to a variety of etiologies with ischemic heart disease being the most common. Some CHF patients suffer from some degree of AV block or are chronotropically deficient such that their cardiac output can be improved with conventional bradycardia pacing. Such pacing, however, may result in some degree of uncoordination in atrial and/or ventricular contractions due to the way in which pacing excitation is typically spread throughout the myocardium without the benefit of the heart's specialized conduction system. The resulting diminishment in cardiac output may be significant in a CHF patient whose cardiac output is already compromised. Intraventricular and/or interventricular conduction defects (e.g., bundle branch blocks) are also commonly found in CHF patients. In order to treat these problems, cardiac rhythm management devices have been developed which provide pacing stimulation to one or more heart chambers in an attempt to improve the coordination of atrial and/or ventricular contractions, termed cardiac resynchronization therapy.

Cardiac resynchronization therapy is pacing stimulation applied to one or more heart chambers in a manner that restores or maintains synchronized bilateral contractions of the atria and/or ventricles and thereby improves pumping efficiency. Certain patients with conduction abnormalities may experience improved cardiac synchronization with conventional single-chamber or dual-chamber pacing as described above. For example, a patient with left bundle branch block may have a more coordinated contraction of the ventricles with a pace than as a result of an intrinsic contraction. In that sense, conventional bradycardia pacing of an atrium and/or a ventricle may be considered as resynchronization therapy. Resynchronization pacing, however, may also involve pacing both ventricles and/or both atria in accordance with a synchronized pacing mode as described below. A single chamber may also be resynchronized to compensate for intra-atrial or intra-ventricular conduction delays by delivering paces to multiple sites of the chamber.

It is advantageous to deliver resynchronization therapy in conjunction with one or more synchronous bradycardia pacing modes, such as are described above. One atrial and/or one ventricular pacing sites are designated as rate sites, and paces are delivered to the rate sites based upon pacing and sensed intrinsic activity at the site in accordance with the bradycardia pacing mode. In a single-chamber bradycardia pacing mode, for example, one of the paired atria or one of the ventricles is designated as the rate chamber. In a dual-chamber bradycardia pacing mode, either the right or left atrium is selected as the atrial rate chamber and either the right or left ventricle is selected as the ventricular rate chamber. The heart rate and the escape intervals for the pacing mode are defined by intervals between sensed and paced events in the rate chambers only. Resynchronization therapy may then be implemented by adding synchronized pacing to the bradycardia pacing mode where paces are delivered to one or more synchronized pacing sites in a defined time relation to one or more selected sensing and pacing events that either reset escape intervals or trigger paces in the bradycardia pacing mode. Multiple synchronized sites may be paced through multiple synchronized sensing/pacing channels, and the multiple synchronized sites may be in the same or different chambers as the rate site.

In bilateral synchronized pacing, which may be either biatrial or biventricular synchronized pacing, the heart chamber contralateral to the rate chamber is designated as a synchronized chamber. For example, the right ventricle may be designated as the rate ventricle and the left ventricle designated as the synchronized ventricle, and the paired atria may be similarly designated. Each synchronized chamber is then paced in a timed relation to a pace or sense occurring in the contralateral rate chamber.

One synchronized pacing mode may be termed offset synchronized pacing. In this mode, the synchronized chamber is paced with a positive, negative, or zero timing offset as measured from a pace delivered to its paired rate chamber, referred to as the synchronized chamber offset interval. The offset interval may be zero in order to pace both chambers simultaneously, positive in order to pace the synchronized chamber after the rate chamber, or negative to pace the synchronized chamber before the rate chamber. One example of such pacing is biventricular offset synchronized pacing where both ventricles are paced with a specified offset interval. The rate ventricle is paced in accordance with a synchronous bradycardia mode which may include atrial tracking, and the ventricular escape interval is reset with either a pace or a sense in the rate ventricle. (Resetting in this context refers to restarting the interval in the case of an LRL ventricular escape interval and to stopping the interval in the case of an AVI.) Thus, a pair of ventricular paces are delivered after expiration of the AVI escape interval or expiration of the LRL escape interval, with ventricular pacing inhibited by a sense in the rate ventricle that restarts the LRL escape interval and stops the AVI escape interval. In this mode, the pumping efficiency of the heart will be increased in some patients by simultaneous pacing of the ventricles with an offset of zero. However, it may be desirable in certain patients to pace one ventricle before the other in order to compensate for different conduction velocities in the two ventricles, and this may be accomplished by specifying a particular positive or negative ventricular offset interval.

Another synchronized mode is triggered synchronized pacing. In one type of triggered synchronized pacing, the synchronized chamber is paced after a specified trigger interval following a sense in the rate chamber, while in another type the rate chamber is paced after a specified trigger interval following a sense in the synchronized chamber. The two types may also be employed simultaneously. For example, with a trigger interval of zero, pacing of one chamber is triggered to occur in the shortest time possible after a sense in the other chamber in order to produce a coordinated contraction. (The shortest possible time for the triggered pace is limited by a sense-to-pace latency period dictated by the hardware.) This mode of pacing may be desirable when the intra-chamber conduction time is long enough that the pacemaker is able to reliably insert a pace before depolarization from one chamber reaches the other. Triggered synchronized pacing can also be combined with offset synchronized pacing such that both chambers are paced with the specified offset interval if no intrinsic activity is sensed in the rate chamber and a pace to the rate chamber is not otherwise delivered as a result of a triggering event. A specific example of this mode is ventricular triggered synchronized pacing where the rate and synchronized chambers are the right and left ventricles, respectively, and a sense in the right ventricle triggers a pace to the left ventricle and/or a sense in the left ventricle triggers a pace to the right ventricle.

As with other synchronized pacing modes, the rate chamber in a triggered synchronized pacing mode can be paced with one or more synchronous bradycardia pacing modes. If the rate chamber is controlled by a triggered bradycardia mode, a sense in the rate chamber sensing channel, in addition to triggering a pace to the synchronized chamber, also triggers an immediate rate chamber pace and resets any rate chamber escape interval. The advantage of this modal combination is that the sensed event in the rate chamber sensing channel might actually be a far-field sense from the synchronized chamber, in which case the rate chamber pace should not be inhibited. In a specific example, the right and left ventricles are the rate and synchronized chambers, respectively, and a sense in the right ventricle triggers a pace to the left ventricle. If right ventricular triggered pacing is also employed as a bradycardia mode, both ventricles are paced after a right ventricular sense has been received to allow for the possibility that the right ventricular sense was actually a far-field sense of left ventricular depolarization in the right ventricular channel. If the right ventricular sense were actually from the right ventricle, the right ventricular pace would occur during the right ventricle's physiological refractory period and cause no harm.

As mentioned above, certain patients may experience some cardiac resynchronization from the pacing of only one ventricle and/or one atrium with a conventional bradycardia pacing mode. It may be desirable, however, to pace a single atrium or ventricle in accordance with a pacing mode based upon senses from the contralateral chamber. This mode, termed synchronized chamber-only pacing, involves pacing only the synchronized chamber based upon senses from the rate chamber. One way to implement synchronized chamber-only pacing is to pseudo-pace the rate chamber whenever the synchronized chamber is paced before the rate chamber is paced, such that the pseudo-pace inhibits a rate chamber pace and resets any rate chamber escape intervals. Such pseudo-pacing can be combined with the offset synchronized pacing mode using a negative offset to pace the synchronized chamber before the rate chamber and thus pseudo-pace the rate chamber, which inhibits the real scheduled rate chamber pace and resets the rate chamber pacing escape intervals. One advantage of this combination is that sensed events in the rate chamber will inhibit the synchronized chamber-only pacing, which may benefit some patients by preventing pacing that competes with intrinsic activation (i.e., fusion beats). Another advantage of this combination is that rate chamber pacing can provide backup pacing when in a synchronized chamber-only pacing mode, such that when the synchronized chamber pace is prevented, for example to avoid pacing during the chamber vulnerable period following a prior contraction, the rate chamber will not be pseudo-paced and thus will be paced upon expiration of the rate chamber escape interval. Synchronized chamber-only pacing can be combined also with a triggered synchronized pacing mode, in particular with the type in which the synchronized chamber is triggered by a sense in the rate chamber. One advantage of this combination is that sensed events in the rate chamber will trigger the synchronized chamber-only pacing, which may benefit some patients by synchronizing the paced chamber contractions with premature contralateral intrinsic contractions.

An example of synchronized chamber-only pacing is left ventricle-only synchronized pacing where the rate and synchronized chambers are the right and left ventricles, respectively. Left ventricle-only synchronized pacing may be advantageous where the conduction velocities within the ventricles are such that pacing only the left ventricle results in a more coordinated contraction by the ventricles than with conventional right ventricular pacing or biventricular pacing. Left ventricle-only synchronized pacing may be implemented in inhibited demand modes with or without atrial tracking, similar to biventricular pacing. A left ventricular pace is then delivered upon expiration of the AVI escape interval or expiration of the LRL escape interval, with left ventricular pacing inhibited by a right ventricular sense that restarts the LRL escape interval and stops the AVI escape interval.

In the synchronized modes described above, the rate chamber is synchronously paced with a mode based upon detected intrinsic activity in the rate chamber, thus protecting the rate chamber against paces being delivered during the vulnerable period. In order to provide similar protection to a synchronized chamber or synchronized pacing site, a synchronized chamber protection period (SCPP) may be provided. (In the case of multi-site synchronized pacing, a similar synchronized site protection period may be provided for each synchronized site.) The SCPP is a programmed interval which is initiated by sense or pace occurring in the synchronized chamber during which paces to the synchronized chamber are inhibited. For example, if the right ventricle is the rate chamber and the left ventricle is the synchronized chamber, a left ventricular protection period LVPP is triggered by a left ventricular sense which inhibits a left ventricular pace which would otherwise occur before the escape interval expires. The SCPP may be adjusted dynamically as a function of heart rate and may be different depending upon whether it was initiated by a sense or a pace. The SCPP provides a means to inhibit pacing of the synchronized chamber when a pace might be delivered during the vulnerable period or when it might compromise pumping efficiency by pacing the chamber too close to an intrinsic beat. In the case of a triggered mode where a synchronized chamber sense triggers a pace to the synchronized chamber, the pacing mode may be programmed to ignore the SCPP during the triggered pace. Alternatively, the mode may be programmed such that the SCPP starts only after a specified delay from the triggering event, which allows triggered pacing but prevents pacing during the vulnerable period.

In the case of synchronized chamber-only synchronized pacing, a synchronized chamber pace may be inhibited if a synchronized chamber sense occurs within a protection period prior to expiration of the rate chamber escape interval. Since the synchronized chamber pace is inhibited by the protection period, the rate chamber is not pseudo-paced and, if no intrinsic activity is sensed in the rate chamber, it will be paced upon expiration of the rate chamber escape intervals. The rate chamber pace in this situation may thus be termed a safety pace. For example, in left ventricle-only synchronized pacing, a right ventricular safety pace is delivered if the left ventricular pace is inhibited by the left ventricular protection period and no right ventricular sense has occurred.

As noted above, synchronized pacing may be applied to multiple sites in the same or different chambers. The synchronized pacing modes described above may be implemented in a multi-site configuration by designating one sensing/pacing channel as the rate channel for sensing/pacing a rate site, and designating the other sensing/pacing channels in either the same or the contralateral chamber as synchronized channels for sensing/pacing one or more synchronized sites. Pacing and sensing in the rate channel then follows rate chamber timing rules, while pacing and sensing in the synchronized channels follows synchronized chamber timing rules as described above. The same or different synchronized pacing modes may be used in each synchronized channel.

In any of the resynchronization pacing modes discussed above, the effectiveness of the therapy is increased to the extent that the frequency of pacing is increased. Accordingly, VRR may be employed to increase the pacing frequency in a ventricular resynchronization pacing mode by adjusting the filter coefficients in the manner described above to result in more paced beats. The LRL adjusted by the VRR filter in this case then corresponds to the ventricular rate chamber escape interval.

As described above, ventricular rate regularization involves adjusting the ventricular escape interval in accordance with measured R—R intervals in order to decrease the variability in the overall ventricular rhythm. The closer the length of the escape interval is to the intrinsic R—R interval, however, the greater the probability that a pace will be delivered coincident with an intrinsic beat. Even though ventricular pacing is inhibited by a ventricular sense occurring before expiration of the ventricular escape interval, a ventricular depolarization may begin some distance away from the sensing/pacing electrode in a different ventricle. The depolarization may then not be sensed in time to inhibit the pacing pulse because of the conduction delay before the depolarization wave reaches the sensing electrode. The result is a hemodynamically inefficient fusion beat which counteracts the otherwise beneficial effects of ventricular rate regularization in maintaining hemodynamic stability. In order to minimize this possibility, an intrinsic ventricular activation should be sensed as soon as possible in order to inhibit pacing. In typical heart failure patients with left bundle branch block, for example, the site of earliest ventricular activation is the right ventricle, and a right ventricular sensing channel is necessary to minimize the possibility of a fusion beat even when only the left ventricle is paced. The most flexible configuration is to use biventricular sensing channels so that the earliest activation occurring in either ventricle can be detected and used to inhibit pacing of one or both ventricles.

When the system is configured for VRR and ventricular resynchronization pacing in a synchronized chamber-only mode, a sensing refractory period can be initiated for the sensing channel of the non-paced ventricle by a ventricular pace. During this period, activity sensed by the channel are ignored for purposes of inhibiting and triggering pacing pulses. This sensing refractory period is of a duration sufficient to prevent detection of the depolarization resulting from the pacing pulse and conducted by cardiac tissue to the sensing electrode and can be programmable.

As described above, the R—R interval can be defined as the time between a present ventricular sense and the preceding ventricular sense or ventricular pace, with the instantaneous rate being the reciprocal of the measured interval. With biventricular sensing, either ventricular sensing channel can be used for defining the R—R intervals, but the first detected sense in a cardiac cycle is preferably used. As an approximation to using the first sense, advantage can be taken of the predominance of left bundle branch blocks in the CHF patient population. In these patients, the right ventricle depolarizes before the left ventricle, and using a right ventricular sense to define the R—R interval is a reasonable approximation for the first ventricular sense. This approximation simplifies the VRR and pacing algorithms when right ventricular senses are used to both define R—R intervals for VRR implementation and to define the cardiac cycle for bradycardia and anti-tachycardia pacing.

Alternatively, the R—R interval can be more particularly defined, depending upon whether a uni-ventricular or biventricular pacing mode is being used. In a uni-ventricular pacing mode, the R—R interval can be defined as the time from either a first ventricular sense or pace in the previous cardiac cycle to the first ventricular sense in the current cycle. In a biventricular pacing mode, the R—R interval can be defined as the time from a first ventricular sense of the previous cycle to the first ventricular sense of the current cycle, and as the time from a ventricular pace in the previous cycle to the first ventricular sense in the current cycle where the paced chamber of the previous cycle is the same chamber as the first ventricular sense of the current cycle.

The VRR algorithm adjusts the ventricular escape interval in accordance with measurements of R—R intervals. In uni-ventricular pacing with biventricular sensing, the ventricular escape interval can be defined as the time between a first ventricular sense or pace and a subsequent pace if no intrinsic activity is detected. The ventricular escape interval may be more particularly defined for biventricular pacing modes as the time from the first ventricular sense of the previous cycle to a ventricular pace in the current cycle where the paced chamber of the current cycle is the same chamber as the first ventricular sense of the previous cycle, and as the time from a ventricular pace in the previous cycle to a ventricular pace in the same chamber during the current cycle.

5. Ventricular Rate Regularization with Anti-Tachyarrhythmia Therapy

VRR may employed in ICDs implanted in patients who are prone to ventricular arrhythmias but are not normally in need of either bradycardia or resynchronization pacing. In these cases, the device may detect a ventricular tachyarrhythmia which does not warrant either a defibrillation shock or anti-tachycardia pacing. VRR pacing may then be initiated in order to improve the patient's cardiac output and possibly lessen the chance of a more dangerous tachyarrhythmia occurring. The device may be programmed to deliver the VRR therapy for a specified length of time after each detection of such a tachyarrhythmia.

VRR may also be employed in devices configured to deliver atrial defibrillation shocks in order to both maintain hemodynamic stability and to more safely deliver the shock. In order to avoid the possible induction of ventricular fibrillation, atrial defibrillation shocks should be delivered synchronously with a sensed R wave and after a minimum pre-shock R—R interval. This is done because the ventricle is especially vulnerable to induction of fibrillation by a depolarizing shock delivered at a time too near the end of the preceding ventricular contraction (i.e., close to the T wave on an EKG). Delivering the shock synchronously with a sensed R wave thus moves the shock away from the vulnerable period, but at a very rapid ventricular rhythm, the ventricular beats may be so close together that even synchronously delivered shocks may induce ventricular fibrillation. Shocking should therefore be delayed until the ventricular rhythm is slow enough to safely deliver the defibrillation pulse as determined by measuring the R—R interval. As noted above, however, the intrinsic ventricular rhythm during atrial fibrillation tends to be both rapid and irregular. If the intrinsic rhythm could be slowed and made more predictable, an atrial defibrillation shock could be more safely delivered.

If AV conduction is intact in a patient, atrial fibrillation results in a very rapid and intrinsic ventricular rhythm, and regularizing the ventricular rate improves cardiac output directly through its effect on diastolic filling. Ventricular rate regularization may be applied in this instance with parameter settings such that the ventricles are driven at a rate near the intrinsic rate. The intrinsic ventricular rhythm that occurs during an episode of atrial fibrillation is a result of the chaotically occurring depolarizations occurring in the atria being passed through the AV node to the ventricles. The intrinsic ventricular rate is thus governed by the cycle length of the atrial fibrillation and the refractory period of the AV node. If a ventricular pacing pulse is delivered before the next intrinsic beat occurs, the ventricular depolarization is conducted retrogradely to the AV node causing late depolarization of the AV node during the ventricular beat. The refractory period of the AV node is also delayed, which delays the time before an atrial depolarization can be conducted through the node to result in an intrinsic beat. The effect of the pace is thus to lengthen the time until the next intrinsic beat. Ventricular rate regularization at a pacing rate near the intrinsic ventricular rate during atrial fibrillation thus not only improves hemodynamics, but also increases the probability that a shockable R—R interval will occur.

Although the invention has been described in conjunction with the foregoing specific embodiment, many alternatives, variations, and modifications will be apparent to those of ordinary skill in the art. Such alternatives, variations, and modifications are intended to fall within the scope of the following appended claims.

What is claimed is:

1. A method for operating a cardiac pacemaker, comprising:
   sensing a ventricle designated as a rate chamber through a ventricular sensing channel and generating a ventricular sense upon detection of depolarization occurring in the rate chamber;
   pacing a ventricle contralateral to the rate chamber, designated as a synchronized chamber, at a specified pacing instant defined with respect to expiration of a rate chamber escape interval, wherein the rate chamber escape interval is reset by a rate chamber sense but not reset by a synchronized chamber sense; and,
   decreasing the rate chamber escape interval toward a lower limit value after a ventricular sense and increasing the rate chamber escape interval toward an upper limit value after a ventricular pace.

2. The method of claim 1 further comprising measuring an R13 R interval associated with each ventricular sense, where the R—R interval is defined as a time between the ventricular sense and a preceding ventricular sense or ventricular pace, and wherein the lower limit value is defined as the measured R—R interval multiplied by a scaling factor.

3. The method of claim 2 wherein the rate chamber escape interval is decreased by computing a weighted average of the measured R—R interval multiplied by the scaling factor and the rate chamber escape interval.

4. The method of claim 3 wherein the rate chamber escape interval is decreased in accordance with the measured R—R interval after each ventricular sense.

5. The method of claim 1 wherein the upper limit value corresponds to a base lower rate limit programmed into the pacemaker.

6. The method of claim 5 wherein the rate chamber escape interval is increased by multiplying the rate chamber escape interval by a specified filter coefficient.

7. The method of claim 1 further comprising:
   measuring an R—R interval associated with each ventricular sense, where the R—R interval is defined as a time between the ventricular sense and a preceding ventricular sense or ventricular pace;
   decreasing the rate chamber escape interval after each ventricular sense by computing a weighted average of the measured R—R interval multiplied by a scaling factor and the rate chamber escape interval; and,
   increasing the rate chamber escape interval after each ventricular pace toward the upper limit value by multiplying the escape interval by a specified filter coefficient.

8. The method of claim 7 wherein the scaling factor is selected from values less than one to values greater than one.

9. The method of claim 1 wherein the rate chamber escape interval is reset by a synchronized chamber pace.

10. The method of claim 1 further comprising pacing the rate chamber upon expiration of the rate chamber escape interval.

11. A cardiac rhythm management device, comprising:
    a rate chamber sensing channel for sensing a ventricle designated as a rate chamber and generating a ventricular sense upon detection of a depolarization occurring in the rate chamber;

a ventricular pacing channel for pacing a ventricle contralateral to the rate chamber, designated as a synchronized chamber;

a controller programmed to deliver a ventricular pace to the synchronized chamber at a specified pacing instant defined with respect to expiration of a rate chamber escape interval, wherein the rate chamber escape interval is reset by a rate chamber sense but not reset by a synchronized chamber sense; and, wherein the controller is further programmed to decrease the rate chamber escape interval toward a lower limit value after a ventricular sense and increase the rate chamber escape interval toward an upper limit value after a ventricular pace.

12. The device of claim 11 wherein the controller is programmed to measure an R—R interval associated with each ventricular sense, where the R—R interval is defined as a time between the ventricular sense and a preceding ventricular sense or ventricular pace, and wherein the lower limit value is defined as the measured R—R interval multiplied by a scaling factor.

13. The device of claim 12 wherein the rate chamber escape interval is decreased by computing a weighted average of the measured R—R interval multiplied by the scaling factor and the rate chamber escape interval.

14. The device of claim 13 wherein the rate chamber escape interval is decreased in accordance with the measured R—R interval after each ventricular sense.

15. The device of claim 11 wherein the upper limit value corresponds to a base lower rate limit programmed into the device.

16. The device of claim 11 wherein the controller is programmed to increase the rate chamber escape interval by multiplying the rate chamber escape interval by a specified filter coefficient.

17. The device of claim 11 wherein the controller is programmed to measure an R—R interval associated with each ventricular sense, where the R—R interval is defined as a time between the ventricular sense and a preceding ventricular sense or ventricular pace;

decrease the rate chamber escape interval after each ventricular sense toward the lower limit value by computing a weighted average of the measured R—R interval multiplied by a scaling factor and the rate chamber escape interval; and, increase the rate chamber escape interval after each ventricular pace toward the upper limit value by multiplying the escape interval by a specified filter coefficient.

18. The device of claim 17 wherein the scaling factor is selectable from values less than one to values greater than one.

19. The device of claim 17 further comprising a synchronized chamber sensing channel for sensing the synchronized chamber and generating a synchronized chamber sense upon detection of a depolarization occurring in the synchronized chamber, and wherein the R—R interval is measured with respect to ventricular senses generated in the rate chamber sensing channel only.

20. The device of claim 17 further comprising a synchronized chamber sensing channel for sensing the synchronized chamber and generating a synchronized chamber sense upon detection of a depolarization occurring in the synchronized chamber, and wherein the R—R interval is measured with respect to a ventricular sense generated in either the rate chamber sensing channel or the synchronized chamber sense, whichever occurs earliest during a cardiac cycle.

21. The device of claim 11 wherein the rate chamber escape interval is reset by a synchronized chamber pace.

22. The device of claim 11 further comprising a pacing channel for pacing the rate chamber and wherein the controller is programmed to deliver a pace to the rate chamber upon expiration of the rate chamber escape interval.

23. The device of claim 11 further comprising a synchronized chamber sensing channel for sensing the synchronized chamber and generating a synchronized chamber sense upon detection of a depolarization occurring in the synchronized chamber.

* * * * *

UNITED STATES PATENT AND TRADEMARK OFFICE
CERTIFICATE OF CORRECTION

| | |
|---|---|
| PATENT NO. | : 7,142,915 B2 |
| APPLICATION NO. | : 10/462029 |
| DATED | : November 28, 2006 |
| INVENTOR(S) | : Kramer et al. |

It is certified that error appears in the above-identified patent and that said Letters Patent is hereby corrected as shown below:

In column 14, line 24, in Claim 2, delete "R13 R" and insert -- R–R --, therefor.

Signed and Sealed this

Thirteenth Day of March, 2007

JON W. DUDAS
*Director of the United States Patent and Trademark Office*